United States Patent [19]

Cracauer et al.

[11] Patent Number: 5,628,753
[45] Date of Patent: May 13, 1997

[54] GASTROSTOMY TUBE REMOVAL TOOL

[75] Inventors: Raymond F. Cracauer, Plymouth; Lester D. Michels, Eden Prairie, both of Minn.

[73] Assignee: Sandoz Nutrition Ltd.

[21] Appl. No.: 457,641

[22] Filed: Jun. 1, 1995

[51] Int. Cl.⁶ .......................... A61F 11/00; A61M 5/178; A61M 5/00
[52] U.S. Cl. .......................... 606/108; 604/158; 604/166; 604/171
[58] Field of Search .......................... 606/185, 186, 606/187, 131, 132, 133, 117, 108, 1; 604/57, 59, 61, 158, 166, 171; 227/134, 176, 177

[56] References Cited

U.S. PATENT DOCUMENTS

| | | |
|---|---|---|
| 4,862,891 | 9/1989 | Smith . |
| 4,966,587 | 10/1990 | Baumgart . |
| 5,112,308 | 5/1992 | Olsen et al. . |
| 5,112,310 | 5/1992 | Grabe .......................... 604/175 |
| 5,139,486 | 8/1992 | Moss .......................... 604/158 |
| 5,391,156 | 2/1995 | Hildwein et al. .......................... 604/164 |

OTHER PUBLICATIONS

Derwent Abstract No. 95–031389 (Dec. 28, 1994).
Derwent Abstract No. 86–037350 (Dec. 20, 1985).

*Primary Examiner*—Robert A. Hafer
*Assistant Examiner*—Benjamin Koo
*Attorney, Agent, or Firm*—Robert S. Honor; Carl W. Battle

[57] ABSTRACT

A gastrostomy feeding tube removal device is comprised of a hollow cylindrical body, a conical head formed at one end and preferably a cap or top at the other to assist in grasping the tool during use. A sheath covers the remaining body portion and is slideably moveable thereon. In use, the gastrostomy tube is pulled through the device which enters the stomach through an ostomy of the patient. Upon contacting the retention bolster means proximate the inner stomach lining, the plastic sheath is pressed forward against the extended members of the retention means thereby collapsing them and withdrawing them into the sheath. The device is then withdrawn from the patient's body simultaneously removing the tube as well.

8 Claims, 4 Drawing Sheets

GASTROSTOMY TUBE REMOVAL TOOL

FIELD OF THE INVENTION

The present invention relates generally to surgical procedures and medical devices for performing them. More specifically, the present invention pertains to enteral feeding tubes and gastrostomy devices and procedures for their insertion and removal.

BACKGROUND OF THE INVENTION

The use of feeding tubes which provide nutritional formula directly into the stomach of patients who are incapable of swallowing for one reason or another have been well known for years. Many different types have been devised which are commonly inserted into the patient by way of surgery, radiological placement or more recently, percutaneous endoscopic gastrostomy. In some cases an opening is cut into the skin, fascia and stomach wall and the gastrostomy tube is directly placed therein. This required the employment of general anesthesia which added an additional risk factor to the patient's well being.

In percutaneous endoscopic gastrostomy, the general procedure comprises inserting an endoscope into the stomach by way of a patient's mouth and esophagus. The stomach is then inflated and a needle and cannula are inserted through an appropriate site from the skin surface into the stomach wall. A snare is fed into the stomach through the endoscope and is looped about the cannula. A guidewire is fed into the stomach through the cannula and is pulled up through the esophagus and mouth by the snare and endoscope. A gastrostomy catheter is then attached to the guidewire and is pulled down through the mouth, through the esophagus to the stomach by pulling the end of the guidewire that protrudes from the cannula which maintains a small hole made in the stomach with the needle. The catheter is pulled though the hole as well, its passage assisted by means of a tapered dilator at the leading end. The catheter is then held in place by means of a retention means or bolster guard which generally consists of a larger, planar surface area than the catheter and lies flat against the interior of the abdominal wall.

Suitable retention means currently in existence include a radially extending flange element, a collar, cuff or a balloon. Another retention means may be placed externally against the skin where the tube exits the skin in order to better secure the catheter in place. The tube may then be connected to an enteral feeding delivery system and the nutritional formula delivered. Accordingly, a number of variations to this general procedure are described in U.S. Pat. No. 5,080,650 to Hirsch et. al., U.S. Pat. No. 4,900,306 to Quinn et. al. and U.S. Pat. No. 4,861,334 to Nawaz.

The gastrostomy tube generally must be removed at some point either due to the conclusion of the need for gastronomic feeding or if the device needs to be replaced for one reason or another. Obviously, the existence and securement of the retention means to the skin surface and stomach wall prevents any easy external removal thereof without potentially causing damage to the stomach, abdominal fascia and skin. Various techniques have been employed to facilitate the removal procedure. These include cutting the gastrostomy tube at the skin level and retrieving the internally disposed portions endoscopically; cutting the gastrostomy tube at the skin level and allowing the retention means and internal portion of the tube to be expelled by means of excretion through the gastrointestinal tract, and surgically removing the entire tube through the creation of a larger incision.

All these procedures have inherently associated problems. The endoscopic retrieval process places the patient at risk as esophageal tissue damage and blockage of the trachea may result during retraction of the tube and retention collar or flange. The method whereby the system is excreted by way of the gastrointestinal tract runs the risk of intestinal or bowel blockage. Surgical removal always runs the risk of patient trauma, anesthesia overdose and excessive bleeding.

A number of attempts have been made in the art in an effort to make insertion and removal of the gastrostomy tube a more simple, less invasive procedure. U.S. Pat. No. 5,073,166 to Parks et. al. discloses a method and apparatus for the emplacement and removal of a gastrostomy catheter that has retention means consisting of an expandable locking mechanism and a locking ring. The locking mechanism comprises expandable legs or arms that are retracted during insertion of the tube into the body so as to afford the smallest diameter with least resistance. An insertion tool is then used to expand the legs, clamping the tube to the patients skin and stomach. The tube may be removed by again inserting the tool at the appropriate time, contracting the legs about the cylindrical body of the tube so that it is "unlocked" and pulled out and withdrawn from the body.

U.S. Pat. No. 5,356,391 to Stewart discloses and claims a gastrostomy tube with a flexible, internal retention flange comprising a collapsible dome shape which reduces patient trauma and risk during tube insertion and removal. The shape of the dome enables it to conform to the contour of the patients stomach and yet readily collapses when longitudinal pressure is applied through retraction of the tube thereby reducing the diameter of the dome for least resistance.

U.S. Pat. No. 5,112,310 to Grobe discloses a percutaneous endoscopic gastrostomy tube in which the retention means is expandable and integral with the tube and may comprise an inflatable balloon or an expandable and retractable basket for securing the tube to the gastric wall. The balloon may be inflated with air or water after insertion and expands to secure the tube to the wall between it and a collar. The balloon can be deflated thereby reducing its size for retraction and removal of the tube. The basket type retention means consists of a plurality of circumferentially spaced ribs which are attached at one end to the distal end of the tube and at the other end to a slidable collar. When retracted, the diameter of the tube is reduced and the tube may be pressed through an ostomy incision. Expanding the basket clamps the collar against the stomach wall thereby holding the tube in place. The ribs are then retracted once the tube is to be removed.

U.S. Pat. No. 5,074,846 to Clegg et. al. and U.S. Pat. No. 4,795,430 to Quinn et. al. both disclose percutaneous endoscopic ostomy devices in which the tube is percutaneously secured to the liner of the stomach using a balloon or an inflatable cuff, respectively. Deflated, both can be passed into the lumen through a small opening in the stoma created by an ostomy. Inflated, they expand and maximizing the circumference of the tube they press against the stomach wall thereby securing the tube to the body. Once the patient no longer is in need of enteral feeding or tube replacement is required the balloon or cuff may be deflated to minimize the circumference of the tube for easier withdrawal.

None of the prior art retention means provide a universal method for the simple extraction and removal of a wide variety of tubes. Moreover, all of the aforementioned references comprise fairly complex structures which are an integral part of the tube itself and cannot afford the surgeon or enterologist the minimal tubular diameter for least friction and resistance against the stomach wall and fascia upon removal. The integral and complex nature of these structures can lead to inoperative or faulty devices when used which may ultimately prevent the simple retraction of the tube. Balloons may not deflate, baskets may fail to collapse, and collars or domes may become obstructed and fail to fold in. Although seemingly minor, such breakdowns can create major problems when the patient is at risk.

It is an object of the present invention to provide a simple means for the percutaneous extraction or withdrawal of an enteral feeding tube from its secured position within the stomach wall. More specifically, it is an object of the present invention to provide a retention means extractor that is easily inserted in the stoma without causing tissue trauma wherein it readily collapses and captures a wide variety of collar or flange style bolster retention means which are then readily pulled out of the stoma without further damage or tear to the stomach, muscle or skin tissue.

SUMMARY OF THE INVENTION

A gastrostomy feeding tube removal device consists of a hollow cylindrical tube that is open at both ends. One of the ends is substantially conical in shape while the other distal end preferably comprises a cap or top to assist in grasping the tool during use. A plastic sheath covers substantially all of remaining tubular body portion and is slideably moveable thereon. A gastrostomy feeding tube is removed from the body of a patient by inserting the tube in the conical head portion and pulling it through the body. Once the head contacts the extending members of the retention bolster means within the stomach, the plastic sheath slides forward pressing against the retention means until it collapses and is pulled inside the sheath. The tube and tool are then simply withdrawn.

BRIEF DESCRIPTION OF THE DRAWINGS

FIG. I is a side view of the gastrostomy tube removal tool of the present invention.

FIG. II is a full side view of the removal tool as it is initially inserted and pulled down the gastrostomy tube.

Figure 1:
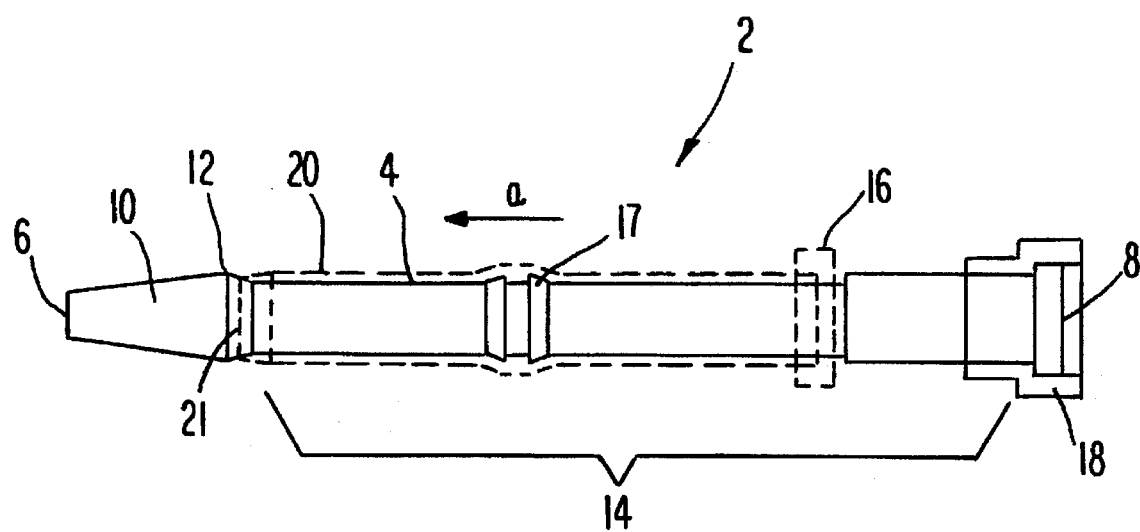

FIG. III is a side view of the removal tool as it contacts the retention means within the stomach.

FIG. IV is a side view of the removal tool as the plastic sheath contacts and collapses the retention means within the stomach wall.

DETAILED DESCRIPTION OF THE INVENTION

Whereas many of the endoscopic gastrostomy feeding tubes of the prior art have collapsible or deflatable retention means which are disclosed as self-removable through the exertion of longitudinally oriented force in the form of retraction, often the collars, flanges, cuffs, buttons and balloons exert too great a degree of resistance against the stomach wall at the ostomy and require additional assistance in order to be easily withdrawn from the stomach of the patient. Other retention bolster means are not self retractable and the means described earlier must be followed for their removal. The present invention is a simple tool and method for the removal of the gastrostomy feeding tube by less drastic and dangerous means.

Retention bolster means of gastrostomy tubes particularly adaptable to the removal process using the tool of the present invention comprise a radial or triangular disk that surrounds the proximal end of the tube or may comprise a plurality of radiating petaloid flanges. Such structures well known in the art and are disclosed in U.S. Pat. Nos. 5,080,650 to Hirsch et. al.; 5,356,391 to Stewart, 4,668,225 to Russo et. al. and 4,826,481 to Sacks et. al. all of which are incorporated herein by reference.

The gastrostomy tube removal tool of the present invention provides the ability to internally collapse the flanges or cuffs of the retention bolster means just prior to retraction of the tube. The cylindrically shaped retractor is provided with a cone-like tip at its one end through which the feeding tube passes. The tapered or cone-shaped head of the tube makes entry into the stoma through the original percutaneous incision easier and with less resistance as the tapered tip gently widens the ostomy in the skin, fascia and stomach wall. With increasing pressure, the retraction tool enters the stomach until the cone's tip presses the top side of the retention bolster flange.

A semi-rigid sheath or tube lies over and is substantially flush with the surface of the removal device and runs along the length thereof. As the device enters the stomach and the proximal edge of the cone-shaped tip presses flush against the top of the flanged or cuff-shaped retention bolster, the semi-rigid sheath is then immediately pressed downward over the cone-shaped tip until it also contacts the side of the flange or cuff of the retention bolster that is flush against the inside wall of stomach. Continued downward pressure of the sheath together with outward traction force applied to the external portion of the gastrostomy tube collapses the flange or cuff members which thereby move inward towards the central axis of the tube and retraction device. These then become folded within the sheath and completely contained therein. The entire gastrostomy tube and retraction tool may be simply pulled out of the ostomy and the incision is then either surgically closed, allowed to spontaneously close or a new tube inserted in its place if replacement is what is called for.

Referring now to FIG. 1, the gastrostomy tube removal tool (2) of the present invention consists of a central, substantially cylindrical structure (4) with and proximal (6) and distal (8) opening that is contiguously hollow there between. The inside diameter at (6) becomes larger immediately past the opening. This provides a snug fit around the gastrostomy tube at the tip, but reduces friction within the device. The proximal end portion (10) is tapered or cone-shaped so as to facilitate entry of the tool into the ostomy of the patient. In other words, the diameter of the opening of the proximal end (6) is somewhat less than that of the tube at a point located distally therefrom (12). The rest of the body of the central core (14) is substantially cylindrical giving the entire structure a somewhat pencil-like appearance.

The central cylindrical bore (4) of the tool is comprised of a substantially rigid material such as stainless steel, aluminum or some other cost effective alloy or certain plastics or any other material that could impart a rigid structure to the device.

The distal end of the gastrostomy removal device (8) may optionally and preferably include a cap or knob portion (18) which is immovably attached thereto. The cap or knob may be integrally molded or fabricated as a part of the central bore (4) out of metal or plastic or may be a separately attached component. The cap or knob provides a grip for the surgeon or gastroenterologist who is performing the removal procedure to grasp as the tool is pushed into the ostomy and is pulled out with the PEG tube and bolster retention means.

A semi-rigid sheath (20) covers a substantial portion of the central bore (4) not comprising the proximally located conical tip (10) or the cap or knob portion (18). The semi-rigid sheath lies flush against and fits snugly over the body portion of the central bore but is slideably movable along the longitudinal axis of the tool (arrow a) upon the exertion of force in this direction. The sheath becomes the vital operational component of the tool during actual removal of the gastrostomy tube and retention bolster means.

The leading edge of sheath (21) rests behind the taper of the cone. Thus, the tissue of the ostomy which is being dilated as the cone passes through it is not scraped and traumatized by the edge of the sheath.

Once the removal tool (cone tip) is within the ostomy and seated against the retention means, the sheath is advanced by forward pressure and the leading edge deflects and stretches up over the cone. As the sheath progresses forward, the portion in contact with the cone remains in a stretched configuration. This is the reason that the sheath material must be semi-rigid (i.e., deformable) and lubricous so that it may slide over the cone with as little resistance as possible.

Preferably, the distal end of the semi-rigid sheath (16) is formed into a lip or knob which, like the distal end (8) of the central base (4) is used to grasp and push the sheath forward and to hold it in position as the entire removal device is pulled out. In this manner, the lip or knob (16) also serves to stop the sheath (20) from further forward movement when it intercepts and locks into a rib structure (17) formed about the middle of the central bore (4). In this manner, the sheath is prevented from accidentally moving all the way forward and off the proximal end (10) of the removal device.

Figure 2:
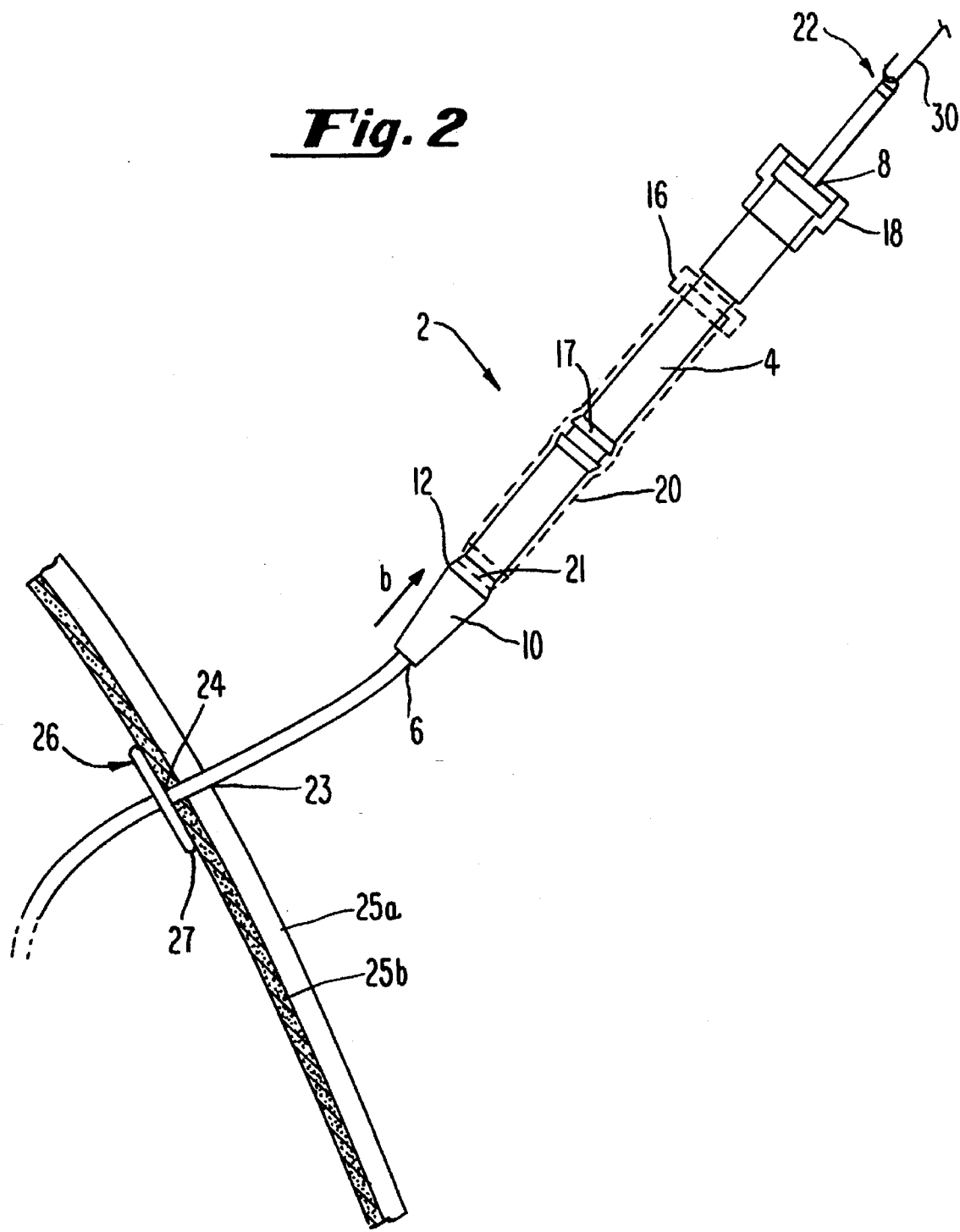
Figure 3:
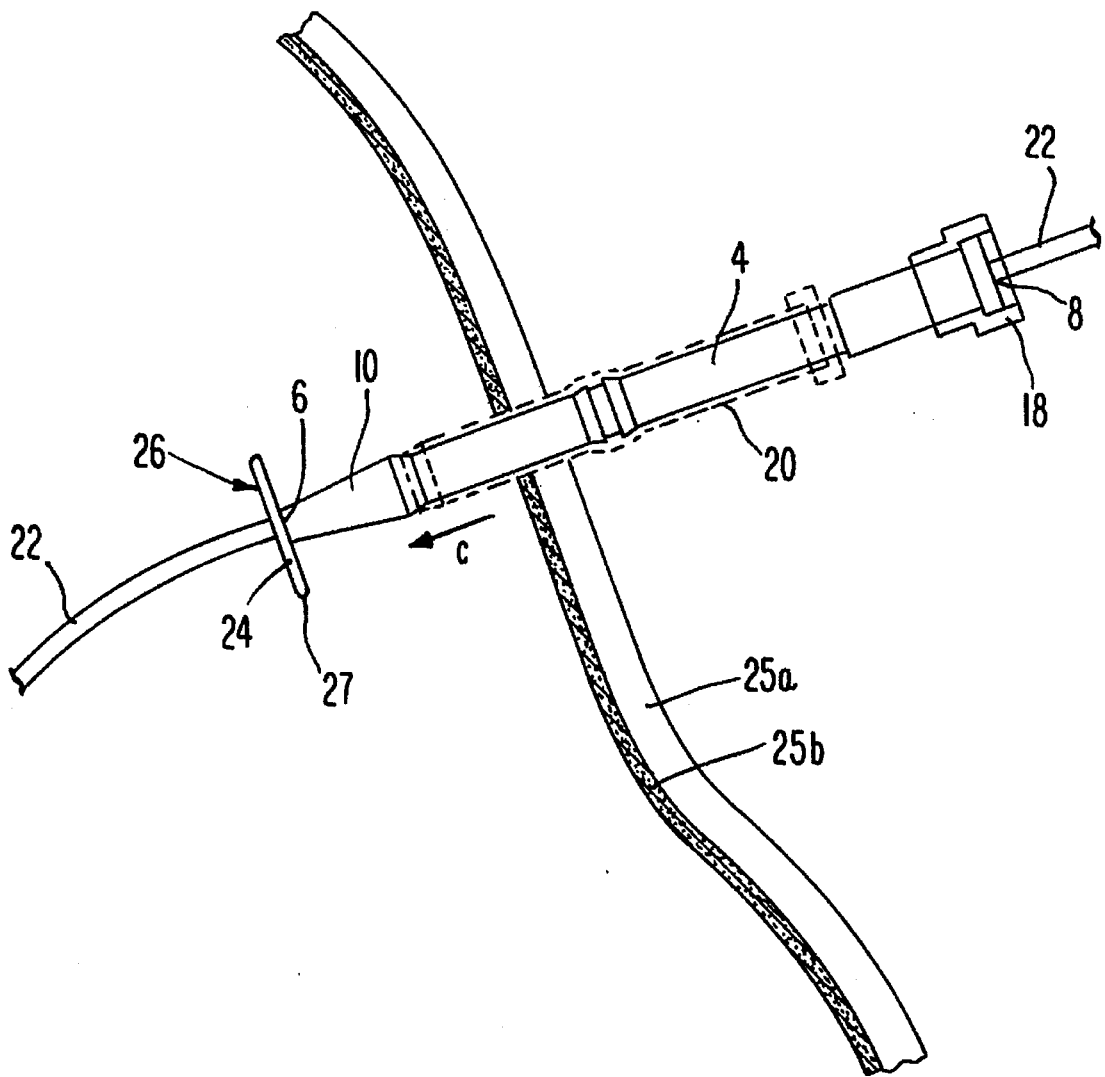
Figure 4:
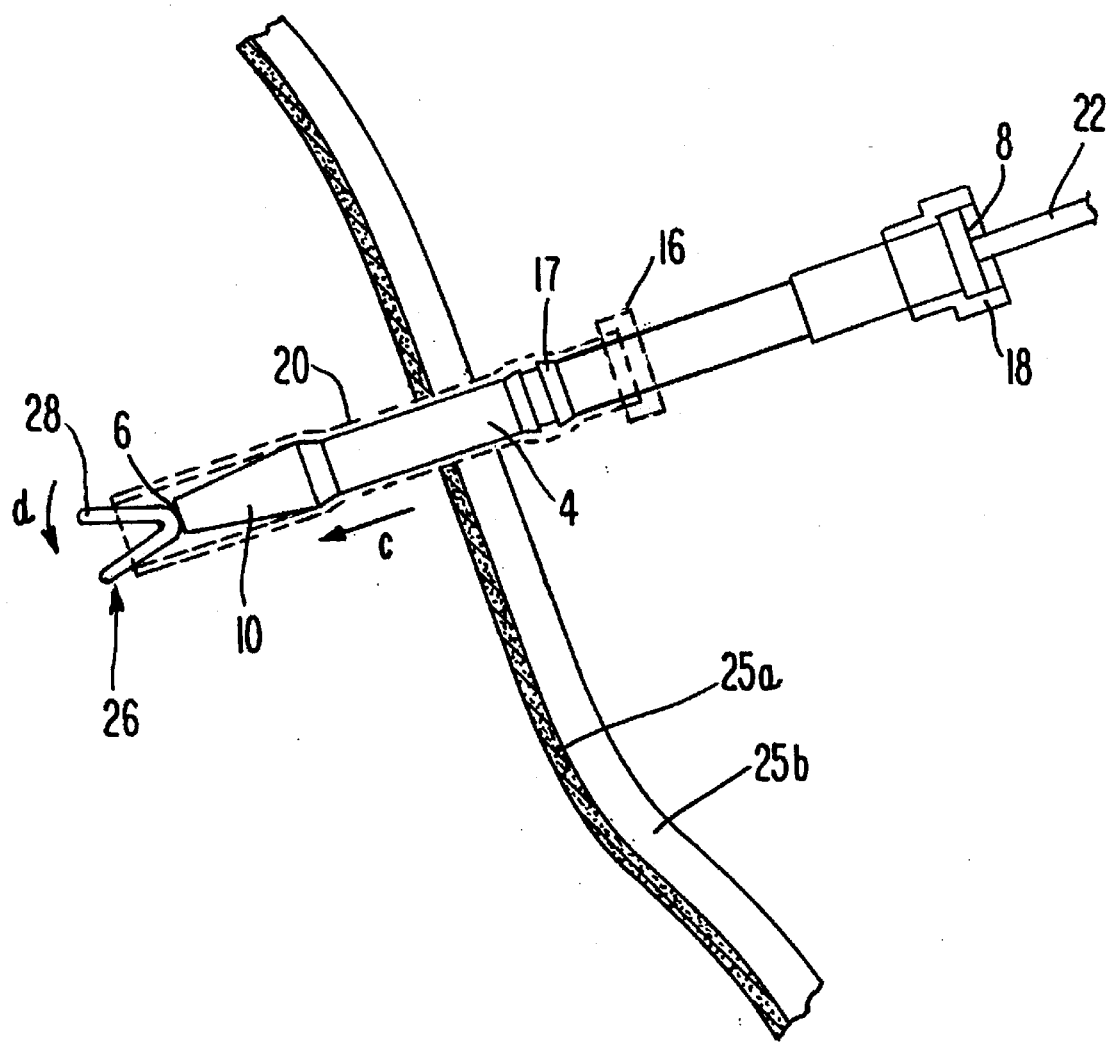

Referring now to FIGS. 2–4, the method for removing the gastrostomy tube and retention means using the device of the present invention is shown. The diameters of the proximal (6) and distal (8) openings are tapered and the central hollow bore or rod (4) diameter is a constant and can be tailored to a specific size of gastrostomy feeding tube as required. Generally, diameters range from 14 French to 28 French. French size measurements are typically used for gastrostomy tubes as is standard in the art. One French equals 1/3 mm.

The procedure is initiated by inserting the external end (21) of the feeding tube (22) that is outside the body within the proximal end (6) of the central bore (4). The tube (22) should be snug or even tight within the bore but should also move slideably through it as shown by arrow (b) upon the exertion of manual force by gently pulling the tube (22) outward along the longitudinal axis of both the tube (22) and central cylindrical bore (4). This process is facilitated, as is known in the art, by the use of an assist device such as a plastic metal hook (30) that can be attached to the end of the feeding tube and can be threaded through the cylindrical bore and used to pull the end of the tube through the bore until it may be grasped as it exits the bore. The tube is gradually pulled through the removal tool (2) out the distal end (8) as the cone-shaped proximal end (10) slowly enters the ostomy in the stomach and fascia walls (25a & b) by gradual dilation of the ostomy to accommodate the tool (sheath) without causing trauma to the tissues. This continues until the proximal tip (6) is flush against the flange cuff or edge (24) of the retention means (26) of the gastrostomy tube (22). See FIG. 3.

As is clearly depicted in FIGS. 2 and 3, the circumference formed by the outer edges (27) of the retention bolster (26) of the gastrostomy tube is considerably greater than that of the proximal end (6) of the central cylinder bore (4). For this reason, as depicted in FIG. 4 the plastic sheath (20) that surrounds and is flush with the surface of the cylindrical rod or bore (4) is urged downward until it also contacts the surface of the retention bolster means within the lining of the stomach (25b). Since the gastrostomy tubing (22) and the integral retention means (26) is comprised of a soft, flexible material as is known in the art, continued lateral pressure (arrow c) against the sheath (20) along the longitudinal axis of the tool body (4) created in part by pulling the external portion of the gastrostomy tube away from the body of the patient forces the flange or cuff element (28) of the retention means (26) backward until the flange collapses inward (arrow d) and is drawn into the sheath (20). Continued exertion of the sheath (20) in this manner pulls the entire retention bolster means (26) completely within the sheath. This captures all expansion forces of the retention bolster within the sheath so that they are not transmitted to the tissues of the ostomy during removal. The tool, retention bolster means and gastrostomy tube can then be easily withdrawn from the stomach out of the ostomy which is then closed either by sutures or natural healing if possible, or filled using a replacement tube.

It is recognized that minor changes or variation may be made to the basic design and method of the present invention which may not have been specifically described herein. It is to be understood that any such changes which do not materially alter the structure or operation of the device are still considered to fall within the spirit and scope of the present invention as recited by the claims that follow.

What we claim is:

1. A gastrostomy tube removal device comprising, combination with a gastrostomy tube having a retention means;
   a. a hollow, rigid, substantially cylindrical body portion with a first proximal open end and a second distal open end,
   b. a tapered, substantially conical portion of said body formed at said proximal end that is adapted to receive gastrostomy tube exiting a patient's body; and
   c. a moveable semi-rigid sheath that is flush with and covers a substantial portion of the remainder of said cylindrical body.

2. The removal device of claim 1 wherein said cylindrical hollow body is adapted to be pulled over the tube until said conical portion of said body contacts at least one radially extending member of a retention means of the gastrostomy tube.

3. The removal device of claim 2 wherein said semi-rigid sheath is moveable over said conical portion of the cylindrical body so as to contact and collapse the at least one extending member of said retention means.

4. The removal device of claim 3 wherein said semi-rigid sheath further comprises a lip or knob formed at the distal end thereof that intercepts and locks with a ribbed flange about the middle of said cylindrical body as the retention means is collapsed.

5. A gastrostomy tube removal device comprising, for use in combination with a gastrostomy tube having a retention means with at least one extending member, a. a hollow, rigid substantially cylindrical body with a first proximal open end and a second distal open end, and;

b. a tapered, substantially conical portion formed at said proximal open end of the body that is adapted to receive said gastrostomy tube exiting a patients body;

c. a semi-rigid sheath that is moveable over the conical portion of the cylindrical body so as to contact and collapse at least one extending member of a retention means of said gastrostomy tube so that said retention means is collapsed and said gastrostomy tube is pulled up into the sheath and the conical portion of said substantially cylindrical body for removal from the patient; and d. said semi-rigid sheath further comprises a lip or knob formed at the distal end thereof that intercepts and locks with a fibbed flange about the middle of said cylindrical body as the retention means is collapsed and the gastrostomy tube removed.

6. The removal device of claim 5 wherein an immovable cap or knob is formed about the distal end of said cylindrical body whose circumference is greater than that of the cylindrical body.

7. The removal device of claim 6 wherein said cap is a substantially circular rim extending outward about the periphery of the distal end portion.

8. The removal device of claim 7 wherein said semi-rigid sheath is comprised of a material selected from the group consisting of polytetrafluoroethylene, polyethylene, polypropylene and other lubricous, simi-rigid plastics and mixtures thereof.

* * * * *